United States Patent [19]

Freeman, Jr.

[11] Patent Number: 4,798,611

[45] Date of Patent: Jan. 17, 1989

[54] ENHANCEMENT OF XENOGENEIC TISSUE

[75] Inventor: Donald C. Freeman, Jr., Newport Beach, Calif.

[73] Assignee: Hancock Jaffe Laboratories, Irvine, Calif.

[21] Appl. No.: 918,280

[22] Filed: Oct. 14, 1986

[51] Int. Cl.$^4$ ................................................ A61F 2/54
[52] U.S. Cl. .......................................... 623/66; 623/1; 623/2; 623/11; 623/13; 128/DIG. 8; 128/898; 8/94.11; 8/94.1 R
[58] Field of Search ............... 8/94.11, 94.1, 94.19 R, 8/94.20; 128/1 R, DIG. 8; 623/1, 2, 11, 13, 66

[56] References Cited

U.S. PATENT DOCUMENTS

| | | | |
|---|---|---|---|
| 3,451,394 | 6/1969 | Bechtol et al. | 8/94.11 |
| 3,453,194 | 7/1969 | Bennett et al. | 204/159.12 |
| 3,823,212 | 7/1974 | Chvapil | 128/DIG. 8 |
| 3,943,045 | 3/1976 | Cordrey et al. | 204/159.22 |
| 4,060,081 | 11/1977 | Yannas et al. | 128/156 |
| 4,223,984 | 9/1980 | Miyata et al. | 128/DIG. 8 |
| 4,400,833 | 8/1983 | Kurland | 623/1 |

OTHER PUBLICATIONS

Collagen Currents, "Effect of Gamma-Radiation on Leather", Jan. 1966, p. 230.

*Primary Examiner*—Richard J. Apley
*Assistant Examiner*—Paul Prebilic

[57] ABSTRACT

Xenogeneic tissue implants prepared by precrosslinking proteins in xenogeneic tissue using, for example, glutaraldehyde, and thereafter irradiating the crosslinked tissue with high energy radiation, e.g. gamma radiation, to sterilize, reduce the immunogenicity and improve the compliance and physical properties of the tissue are disclosed.

8 Claims, No Drawings

ENHANCEMENT OF XENOGENEIC TISSUE

FIELD OF THE INVENTION

This invention relates to xenogeneic tissue implantation in human tissue repair and prostheses.

BACKGROUND OF THE INVENTION

Implantation in humans of xenogeneic tissue, i.e. tissue from a species other than human, has been carried on extensively for more than two decades. Xenogeneic implants are useful in replacing human tissues which are damaged by pathological or traumatic injury. Such implants have been used for replacing heart valves, ligaments, tendons and skin, for example. Many techniques for preparation and treatment of xenogeneic tissue have been developed for many types of prosthetic and tissue repair applications in the human body. For example, treatment of such tissue with collagen in various forms and degrees of denaturization are known (U.S. Pat. Nos. 3,563,228, Seiderman, 3,949,073, Daniels et al, and 4,233,360, Luck, et al.) Treatment of graft tissues with aldehydes, and glutaraldehyde in particular, is well known (see, for example, U.S. Pat. No. 3,988,872, Dardik, et al, which is but one of many disclosures of the use of glutaraldehyde in tissue treatment.)

Exemplary of the state of the art are the following U.S. Pat. Nos.: Angell et al., U.S. Pat. Nos. 4,035,848 and 4,247,292 and Hancock, et al, U.S. Pat. No. 4,050,893—glutaraldehyde treatment of porcine heart valves; Schechter, U.S. Pat. No. 4,120,649—glutaraldehyde treatment of pigskin, human tissue, and amniotic membranes; Holman, et al, U.S. Pat. Nos. 4,239,492 and 4,240,794—glutaraldehyde treatment of umbilical cord tissue for vascular grafts; Ketharanathan, U.S. Pat. No. 4,319,363—glutaraldehyde treatment of artificially induced tubular structure of collagenous tissue; Lentz et al, U.S. Pat. No. 4,323,358—treatment of implant tissue with glutaraldehyde and wetting agent; Wright, U.S. Pat. No. 4,350,492, and Lane, U.S. Pat. Nos. 4,372,743 and 4,443,895—heart valve prosthesis from glutaraldehyde treated porcine heart valve; Kurland, U.S. Pat. No. 4,400,833—tendons and ligaments from cows and pericardium or other porcine tissue treated with glutaraldehyde and reinforced with synthetic mesh structure; Pollock, et al, U.S. Pat. No. 4,402,697—treatment of implant tissue with phosphate ester and glutaraldehyde; and Pollock, U.S. Pat. No. 4,405,327—treatment of implant tissue with quaternary ammonium compounds and glutaraldehyde.

One of the major problems which have had to be overcome in the preparation of implant tissues is the histocompatibility barriers which the human recipient erect when a non-self material is introduced. Immune rejection of transplants has been and remains a concern, even though much work has been done in this area of medical-immunochemical technology.

Prevention of or inhibition of infection is another goal in the field of implantation.

As illustrated by the previously cited prior art, glutaraldehyde has been reported as being effective in reducing antigenicity and inhibiting infection of implant tissue. Glutaraldehyde cross-links proteins rapidly and effectively, and causes the cross-linking of proteins in the tissue being treated. This treatment increases resistance to proteolytic cleavage and hence increases resistance to enzymatic degradation. The treatment of implant tissue with glutaraldehyde is sometimes referred to as "tanning" because it crosslinks the protein and inhibits enzymatic and biochemical degradation of the tissue, comparable in general to the effect of tanning leather. Glutaraldehyde is also often used as the preservative in aqueous solution for storing tissues after treatment.

Xenografts prepared by the prior art methods suffer from three principal disadvantages, none of which precludes their use for human implantation, but which, nevertheless, represent deterrents to their greater acceptability for use in human tissue replacement.

First, despite the fact that their primary constituent is only weakly immunogenic, by virtue of collagen being present in all mammalian species, and that the crosslinking process further reduces their immunogenicity, xenografts are capable of stimulating the formation of circulating antibodies in the human system, indicating some residual immunogenicity.

Second, the use of some chemical sterilants increases the risk that toxic response will be encountered in sensitive individuals, even after thorough rinsing of the xenograft prior to implantation.

Third, crosslinked xenografts are somewhat stiffer than the native tissue and this stiffness, or lessened compliance, is undesirable, since the xenograft functions best when it preserves the original biomechanical properties that nature intended for the function of that particular tissue.

A feature of the present invention is that it encompasses methods of radiating pre-crosslinked tissue which reduces, or eliminates, one or all of these three disadvantages.

Collagenous tissue in uncrosslinked form has been reported to be seriously degraded by radiation. Apparently, this reported result has deterred investigators from studying all aspects of radiation treatment of xenogeneic tissue.

SUMMARY OF THE INVENTION

The present invention contemplates, as an article of commerce for use in implantation therapy, a tissue which has been treated to crosslink the proteins, i.e. a cross-linked tissue, and which, thereafter, has been subjected to radiation sufficient to effect sterilization and to reduce immunogenicity and increase compliance, but insufficient to cause significant degradation.

As a method, the present invention comprises the steps of crosslinking proteins in a tissue and thereafter sterilizing the tissue with radiation in an amount sufficient to effect sterilization and to reduce immunogenicity and increase compliance, but insufficient to cause significant degradation.

DESCRIPTION OF THE PREFERRED EMBODIMENT

The method of the present invention is applicable to most and probably all xenogeneic tissue preparation. Examples of the types of xenogeneic tissues which can be prepared by and which results from the present invention include tendons, ligaments, pericardial membrane, skin, umbilical cord membrane, heart valve tissue, vascular tissue and the like.

The first step in the process of preparing the tissues of this invention is to effect crosslinking of the protein in the tissue. Any crosslinking reagent may be used, glutaraldehyde currently being one of the preferred reagents. Other aldehydes, however, or other crosslinking materials may be used.

The crosslinking can be carried out in any desired method. Many such methods are described in the prior art. Generally, the crosslinking step comprises soaking the tissue in glutaraldehyde solution, or other aldehyde containing solution, for from a few minutes to several days, depending upon the rate of crosslinking reaction. The rate of crosslinking reaction can be controlled by controlling the concentration of glutaraldehyde and, to a lesser extent, by controlling the pH and/or the temperature of the crosslinking reagent. The concentration of the glutaraldehyde is typically from about 0.1% to 5.0% The solution is typically buffered to about pH 7 to 9 with any suitable buffer, e.g. conventional bicarbonate, citrate, and phosphate buffers and the like. Time and concentration are, of course, related and considerable variation in both are well known in the art. The solution may include one or a number of crosslinking materials, such as, for example, formaldehyde, glyoxal, and/or dialdehyde starch. This step is, of course, well known and reference may be made to any number of prior art patents and publications for guidance as to this step. For example, one well known treatment method for crosslinking tissue, i.e. crosslinking the proteins in the tissue, is described by Yarbrough, et al; Structural alterations in tissue cardiac valves implanted in patients and in calves., *J Thoracic and Cardiovascular Surgery*, March 1973, pp. 364–74.

The second step of the present process is to irradiate the tissue which has been previously crosslinked as described. It is, of course, well known that sterilization can be accomplished by radiation with high energy photons such as X-rays and gamma rays; however, it is also known that proteins generally and collagen in particular is seriously degraded by such radiation. One would not, therefore, normally consider radiation sterilization for xenogeneic tissue implants.

An optional step may be carried out before the second step just described. In some instances, a chemical sterilization or partial sterilization may be carried out to reduce the bioburden before the irradiation step is performed.

The irradiation step of this invention can be carried out using very high energy X-radiation; however, it is considered preferable and easier to irradiate the pre-crosslinked xenogeneic tissue with gamma radiation such as, for example, from a conventional $Co^{60}$ gamma source.

The amount of radiation is not critical in that some variation is possible, though it is possible to over-irradiate the tissue. In practice, the amount of radiation which first begins significantly to degrade the xenogeneic tissue in which the protein has been substantially crosslinked is determined. This is the upper level of radiation normally employed. The amount of radiation which is just sufficient to sterilize the xenogenic tissue in which the protein has been substantially crosslinked is determined, thus establishing the minimum level of radiation. The preferred range of irradiation is from at least the level or irradiation which is reliable to effect sterilization. In most instances, is desirable to effect two or more, and preferably about two or about five, times the minimum quantity of radiation necessary to effect sterilization, but less than the amount of irradiation which begins significantly to degrade the previously crosslinked xenogeneic tissue. The preferred range of radiation using cobalt-60 gamma radiation is from about two to about eight megarads, usually in the range of from two to five megarads. There are some indications that it is preferable to utilize lower irradiation flux for longer periods of time, as compared with a higher irradiation flux for a shorter period of time, to effect the same quantity of irradiation; however, this phenomenon has not been fully explored.

Radiation is carried out in the conventional manner, i.e. by placing the xenogeneic tissue in which the protein has been substantially crosslinked in a suitable glass or other container, and placing the container adjacent the radiation source and opening a path or slit between the radiation source and the tissue to generally uniformly expose the tissue in the gamma rays emitted by the radioactive decay of $Co^{60}$, or such other gamma ray source, or an equivalent high energy radiation source such as may, for example, result from electron beam acceleration, as may be available.

Effective sterilization is easily determined using conventional microbiologial techniques, such as the inclusion of suitable biological indicators in the radiation batch, as is now conventional, or the older but suitable method of contacting the tissue with a culture medium and incubating the medium to determine sterility of the tissue. These are, of course, textbook methods.

Degradation of the pre-crosslinked xenogeneic tissue by irradiation is also determined using well known and conventional tests and criteria, i.e. reduction in shrink temperature, $T_S$; susceptibility to enzyme attack, e.g. collagenase; extractability of degradation products, e.g. collagen fragments; and decrease in physical properties such as tensile strength.

As expected, radiation sterilization was effective in obviating the need for toxic sterilizing chemicals. Contrary to all expectations, however, the amount of radiation required for sterilization did not degrade the xenogeneic tissue in which the protein has been substantially crosslinked.

Surprisingly, the physical characteristics of the irradiated xenogeneic tissue in which the protein had previously been substantially crosslinked were greatly improved. Tensile strength remain approximately as in the unirradiated tissue, but the irradiated tissue was less rigid, more flexible and compliant and, therefore, superior to the unirradiated tissue for most implant purposes, being much more like the original tissue than the unirradiated tissue.

Another surprising discovery was also made. One would expect that one of the effects of irradiation would be to break some of the crosslinked bonds which had been previously effected in the tissue and, therefore, to expose sites susceptible to enzyme attack and increase the potential antigenicity of the tissue. The contrary was found, however. The antigenicity of the irradiated tissue was reduced. The reduced antigenicity of the irradiated xenogeneic tissue in which the protein had previously been substantially crosslinked was shown by comparing reactivity against collagen-induced antibodies of both animal and human origin.

It is presumed that some crosslinking is broken by the irradiation, but apparently not the crosslinks which would expose sites for enzyme attack or antigenic determinant sites; however, the precise change which occurs is unknown and unexplainable by an hypothesis of which the inventor is aware, as the results are most unexpected and run contrary to the conventional wisdom of the crosslinked tissue art.

Treatment of bovine tendon is given to exemplify the invention, for, as previously explained, the source of nature of the tissue is not critical and virtually any tissue may be treated and used according to this invention. Any suitable bovine tendon is cleaned, excess tissue, fat, etc. is removed and, generally, is prepared in the manner in which xenografts are conventionally prepared. The bovine tendon tissue is then pre-crosslinked, either free-floating or in a fixed configuration as desired, in glutaraldehyde, or other crosslinking reagent, as described above and in the prior art, e.g. as described by Yarbrough, et al, supra.

The pre-crosslinked bovine tendon thus prepared is placed in sterile physiological buffered saline solution in a glass or other container and the container is exposed to from two or five magarads of sterilizing high energy radiation, typically gamma radiation from $Co^{60}$. Sterilization is assured by appropriate control or testing, and the tissue is checked to assure that no significant degradation has occurred, using the methods described. The container may then be stored indefinitely and, when used, need only be removed from the container and implanted.

As another example, by way of illustration, and not of limitation, fresh bovine or porcine diaphragm tissue is received from the slaughter house, inspected to meet vendor specifications, and thoroughly rinsed in pH 7.4 phosphate buffered solution. The diaphragm tissue is dissected, separating and discarding all fat tissue and extraneous connective tissue and blood vessels, to leave only a smooth serous side and a fibrous side. The fibrous side is thinned down to a maximum of 0.5 mm using pathology scalpels. The dissected tissue is cut into smaller pieces of usable areas. This tissue, which retains its natural structure, i.e. is not comminuted or disintegrated and reconstituted, is submerged in a suitable container of 0.2% phosphate buffered glutaraldehyde pH 7.4 and kept at room temperature. The submerged tissue is laid flat in the container and left unstressed. The container is kept closed to eliminate the possibility of contamination to the tissues, and Good Laboratory Practice Regulations and Good Manufacturing Practice Regulations are followed at all phases of the process. After 24 hours has elapsed, the tissue is turned and the solution discarded and fresh 0.2% buffered glutaraldehyde is added until the tissue is completely submerged. This procedure is repeated at 48 and 72 hours. After 72 to 96 hours, samples of the crosslinked tissue are tested using standard Shrinkage Temperature testing apparatus and procedures to assure adequate crosslinking. The crosslinked tissue is aseptically dissected to final configuration under sterile environment, such as, for example, a Class 100 Laminar Flow Bench. The final dimensions will depend upon the particular patient and procedure for which the tissue is being prepared. A series of tissues range in size may be prepared thus permitting the surgeon to select the appropriate size. The surgeon can, of course, modify a given size to meet a particular requirement as determined during surgery. The tissue is inspected by Quality Assurance to assure compliance with all specifications, packaged in an approved container of sterile physiologic saline and radiation sterilized and treated as described.

There are, of course, many variables which are controlled according to well known principles and prior art practices, and which may be adjusted and varied without departing from the scope of this invention.

INDUSTRIAL APPLICATION

The tissues of the invention are suitable for shipment and sale as human implants.

What is claimed is:

1. The method of preparing a xenogeneic tissue from animal tissue structures such as tendons, ligaments, pericardial membrane, skin, umbilical cord, and the like, without disintegration or comminution and reconstitution, for implantation comprising the steps of:
   (a) removing excess tissue and fat from a tissue structure of an animal;
   (b) cutting the tissue structure to a desired size and configuration;
   (c) treating the tissue structure resulting from the preceding steps (a) and (b) with a chemical crosslinking reagent to effect cross-linking of the tissue constituents; and, thereafter
   (d) irradiating the tissue structure resulting from step (c) with high energy X-radiation or gamma radiation with from about two times to about five times the amount of such radiation as is necessary to sterilize said tissue structure, said amount of radiation being sufficient to sterilize the tissue structure but less than the amount of radiation which significantly (i) reduces shrink temperature $T_s$, (ii) increases the extractability of degradation products, and (iii) decreases the tensile strength of the tissue structure, and which renders the tissue structure more flexible and compliant, and less antigenic than the unirradiated tissue structure.

2. The method of claim 1 wherein the tissue is irradiated with from about two to about eight megarads of gamma radiation.

3. The process of claim 1 wherein the chemical cross-linking reagent is glutaraldehyde.

4. The method of claim 3 wherein the tissue is irradiated with from about two to about eight megarads of gamma radiation.

5. A xenogeneic graft tissue prepared from animal tissue structures such as tendons, ligaments, pericardial membrane, skin, umbilical cord, and the like, comprising the steps of:
   (a) removing excess tissue and fat from a tissue structure of an animal and cutting the tissue to a desired size and configuration, all without disintegrating or comminuting the tissue;
   (b) treating the tissue from step (a) with a chemical crosslinking reagent to effect cross-linking of the tissue constituents, and
   (c) treating the tissue structure from step (b) with high energy X-radiation or gamma radiation with from about two times to about five times the amount of such radiation as is necessary to sterilize said tissue structure, said amount of radiation being sufficient to sterilize the tissue structure but less than the amount of radiation which significantly (i) reduces shrink temperature $T_s$, (ii) increases the extractability of degradation products, and (iii) decreases the tensile strength of the tissue structure, and which renders the tissue structure more flexible and compliant, and less antigenic than the unirradiated tissue structure.

6. The tissue of claim 5 wherein the irradiation is with from about two to about eight megarads of gamma radiation.

7. The tissue of claim 6 wherein the cross-linking is carried out with glutaraldehyde.

8. The tissue of claim 5 wherein the cross-linking is carried out with glutaraldehyde.

* * * * *